(12) United States Patent
Russo et al.

(10) Patent No.: US 11,697,674 B2
(45) Date of Patent: Jul. 11, 2023

(54) HUMAN CHORIONIC GONADOTROPIN VARIANT PEPTIDES AND TREATMENT OF BREAST CANCER

(71) Applicant: Institute For Cancer Research, Philadelphia, PA (US)

(72) Inventors: Jose Russo, Philadelphia, PA (US); Yanrong Su, Philadelphia, PA (US); Julia Santucci Pereira Del Buono, Philadelphia, PA (US); Mark Andrake, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 275 days.

(21) Appl. No.: 16/756,191

(22) PCT Filed: Oct. 15, 2018

(86) PCT No.: PCT/US2018/055841
§ 371 (c)(1),
(2) Date: Apr. 15, 2020

(87) PCT Pub. No.: WO2019/079167
PCT Pub. Date: Apr. 25, 2019

(65) Prior Publication Data
US 2021/0188935 A1  Jun. 24, 2021
US 2022/0041679 A9  Feb. 10, 2022

Related U.S. Application Data

(60) Provisional application No. 62/572,615, filed on Oct. 16, 2017.

(51) Int. Cl.
C07K 14/59   (2006.01)
A61K 47/69   (2017.01)
A61K 31/138  (2006.01)
A61K 38/24   (2006.01)
A61K 31/706  (2006.01)

(52) U.S. Cl.
CPC .......... C07K 14/59 (2013.01); A61K 31/138 (2013.01); A61K 31/706 (2013.01); A61K 38/24 (2013.01); A61K 47/6929 (2017.08)

(58) Field of Classification Search
CPC .... C07K 14/59; A61K 31/138; A61K 31/706; A61K 38/24; A61K 47/6929; A61K 45/06; A61K 38/00
See application file for complete search history.

(56) References Cited

U.S. PATENT DOCUMENTS

2009/0209453 A1   8/2009  Moyle
2013/0064882 A1*  3/2013  Russo .................. A61P 35/00
                                            514/19.5
2015/0064236 A1   3/2015  Bancel et al.

FOREIGN PATENT DOCUMENTS

WO   2009089102    7/2009
WO   2009108917    9/2009
WO   2011127380   10/2011
WO   2014068408    5/2014
WO   2020071912    4/2020

OTHER PUBLICATIONS

Susanne Schüler-Toprak, Human Chorionic Gonadotropin and Breast Cancer, Int. J. Mol. Sci. 2017, 18, 1587; doi:10.3390/ijmsl 8071587.*
Uniprot Protein Databse, P0DN86 • CGB3_HUMANUniprot Protein Database, accessed on Jul. 14, 2022.*
International Search Report and Written Opinion for PCT Application PCT/US2018/055841.

* cited by examiner

*Primary Examiner* — Julie Ha
*Assistant Examiner* — Erinne R Dabkowski
(74) *Attorney, Agent, or Firm* — Armstrong Teasdale LLP

(57) ABSTRACT

The present disclosure provides hCG variant proteins, nucleic acid molecules encoding the same, vectors comprising nucleic acid molecules, compositions comprising the same, and methods of treating cancer.

10 Claims, No Drawings

Specification includes a Sequence Listing.

HUMAN CHORIONIC GONADOTROPIN VARIANT PEPTIDES AND TREATMENT OF BREAST CANCER

FIELD

The present disclosure is directed, in part, to hCG variant proteins, nucleic acid molecules encoding the same, vectors comprising nucleic acid molecules, compositions comprising the same, and methods of treating cancer.

BACKGROUND

Human chorionic gonadotropin (hCG) represents one of the four members of the glycoprotein family which also include follitropin (FSH), thyrotropin (TSH) and lutropin (LH). hCG is a heterodimeric consisting of a 92 amino acid α (alpha) subunit and a 145 amino acid β (beta) subunit. The α-subunit is ubiquitous among the four glycoprotein families while the β-subunit is limited to hCG. While hCG is typically produced by syncytiotrophoblasts in the placenta after implantation it is also upregulated in certain cancer tumors in both males and females. In particular, overexpression leading to β-subunit secretion in various cancer cell types has been observed independent of α-subunit gene expression.

Thus, compositions and methods that attenuate hCG production within cancer microenvironments are needed. Likewise, while some cancer therapeutics are useful to modulate cancer in a patient, there remains a need for improved cancer therapeutic compositions and methods which are designed to temper the role of hCG in cancer development and progression ultimately improving patient outcomes.

SUMMARY

The present disclosure provides peptides comprising an amino acid sequence that is at least about 80%, at least about 85%, at least about 90%, at least about 95%, at least about 96%, at least about 97%, at least about 98%, at least about 99%, or 100% identical to the amino acid sequence Xaa-Xaa-Cys-Xaa-Arg-Ser-Xaa-Thr-Asp-Cys-Gly-Gly-Pro-Lys-Asp-His-Pro (SEQ ID NO:1), and pharmaceutical compositions comprising one or more of these peptides and a pharmaceutically acceptable carrier.

The present disclosure also provides nucleic acid molecules comprising a nucleotide sequence that is at least about 80%, at least about 85%, at least about 90%, at least about 95%, at least about 96%, at least about 97%, at least about 98%, or at least about 99% identical to the nucleotide sequence gcgctgtgccgccgcagcaccaccgattgcggcggcccgaaagatcatccg (SEQ ID NO:5), and pharmaceutical compositions comprising one or more of these nucleic acid molecules and a pharmaceutically acceptable carrier.

The present disclosure also provides nucleic acid molecules comprising a nucleotide sequence that is at least about 80%, at least about 85%, at least about 90%, at least about 95%, at least about 96%, at least about 97%, at least about 98%, or at least about 99% identical to the nucleotides sequence gcgctgtgccgccgcagcaccaccgattgcggcggcccgaaagatcatggcagcctgcgcagcaaaa aaaccatgctggtgcagaaaacgtgaccagcgaa (SEQ ID NO:6), and pharmaceutical compositions comprising one or more of these nucleic acid molecules and a pharmaceutically acceptable carrier.

The present disclosure also provides vectors comprising the nucleic acid molecules.

The present disclosure also provides host cells comprising the vectors.

The present disclosure also provides methods for treating a subject having cancer comprising administering to the subject in need thereof at least one peptide or nucleic acid molecule described herein, or a pharmaceutical composition comprising the same, wherein the cancer is selected from the group consisting of breast cancer, prostate cancer, ovarian cancer, uterine cancer, endometrial cancer, brain cancer, and testicular cancer.

DESCRIPTION OF EMBODIMENTS

The terminology used herein is for the purpose of describing particular embodiments only and is not intended to be limiting.

As used herein, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "coding sequence" or "encoding nucleic acid" means the nucleic acids (RNA or DNA molecule) that comprise a nucleotide sequence which encodes an hCG peptide and/or variants. The coding sequence can further include initiation and termination signals operably linked to regulatory elements including a promoter and polyadenylation signal capable of directing expression in the cells of an individual or mammal to which the nucleic acid is administered.

As used herein, "consensus" or "consensus sequence" means a polypeptide sequence based on analysis of an alignment of multiple subtypes of a particular hCG peptide variant. Nucleic acid sequences that encode a consensus polypeptide sequence can be prepared. Peptides comprising hCG peptide variants that comprise consensus sequences and/or nucleic acid molecules that encode such peptides can be used to induce broad anti-cancer properties against multiple subtypes or serotypes of a particular cancer.

As used herein, "electroporation" means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, "fragment" with respect to nucleic acid sequences, means a nucleic acid sequence or a portion thereof, that encodes a portion of an hCG peptide and/or variant capable of eliciting an anti-cancer response in a mammal that cross reacts with a full length wild type hCG peptide. The fragments can be DNA fragments selected from at least one of the various nucleotide sequences that encode protein fragments set forth below.

As used herein, "fragment" or "variant" with respect to polypeptide sequences, means a portion of an hCG peptide capable of eliciting an anti-cancer response in a mammal. Fragments of consensus or wild type hCG peptides can comprise at least 10%, at least 20%, at least 30%, at least 40%, at least 50%, at least 60%, at least 70%, at least 80%, at least 90% or at least 95% of a consensus or wild type hCG peptide and/or variants. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus or wild type protein.

As used herein, "genetic construct" refers to the DNA or RNA molecules that comprise a nucleotide sequence which encodes an hCG peptide and/or variants thereof. The coding sequence includes initiation and termination signals operably linked to regulatory elements including a promoter and polyadenylation signal capable of directing expression in the cells of the individual to whom the nucleic acid molecule is administered.

As used herein, "expressible form" refers to gene constructs that contain the necessary regulatory elements operable linked to a coding sequence that encodes an hCG peptide and/or variants such that when present in the cell of the individual, the coding sequence will be expressed.

As used herein, "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous" refers to a probe that can hybridize to a strand of the double-stranded nucleic acid sequence under conditions of low stringency. When used in reference to a single-stranded nucleic acid sequence, the term "substantially homologous" refers to a probe that can hybridize to (i.e., is the complement of) the single-stranded nucleic acid template sequence under conditions of low stringency.

As used herein, "identical" or "identity" in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) residues can be considered equivalent. Identity can be performed manually or by using a computer sequence algorithm such as BLAST or BLAST 2.0. Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Any amino acid or nucleotide number calculated as a % identity can be rounded up or down, as the case may be, to the closest whole number.

As used herein, "human chorionic gonadotropin peptide variants" means a peptide which may be an isolated peptide, synthesized, or a peptide that forms part of a protein with other peptides.

As used herein, "nucleic acid" or "oligonucleotide" or "polynucleotide" means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

As used herein, "operably linked" means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

As used herein, "promoter" means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, "signal peptide" and "leader sequence", used interchangeably, refer to an amino acid sequence that can be linked at the amino terminus of an hCG peptide and/or variant set forth herein. Signal peptides/leader sequences typically direct localization of a protein. Signal peptides/leader sequences used herein can facilitate secretion of the protein from the cell in which it is produced or anchor it in the membrane. Signal peptides/leader sequences are often cleaved from the remainder of the protein, often referred to as the mature protein, upon secretion from the cell. Signal peptides/leader sequences are linked at the N terminus of the protein.

As used herein, "stringent hybridization conditions" means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 to 10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01 to 1.0 M sodium ion concentration (or other salts) at pH 7.0 to 8.3 and the temperature is at least about 30° C. for short probes (e.g., about 10 to 50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, "substantially complementary" means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used herein, "substantially identical" means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, "variant" with respect to a nucleic acid means: i) a portion or fragment of a referenced nucleotide sequence; ii) the complement of a referenced nucleotide sequence or portion thereof; iii) a nucleic acid that is substantially identical to a referenced nucleic acid or the complement thereof; or iv) a nucleic acid that hybridizes under stringent conditions to the referenced nucleic acid, complement thereof, or a sequences substantially identical thereto.

As used herein, "variant" with respect to a peptide or polypeptide means that it differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change Amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "vector" means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector.

The present disclosure provides hCG variant peptides, the nucleic acid sequences that encode them and pharmaceutical compositions comprising the same that can be used to treat various forms of cancer.

The present disclosure provides peptides that comprise at least one or more hCG peptide variants.

The present disclosure provides peptides comprising an amino acid sequence that is at least about 80%, at least about 85%, at least about 90%, at least about 95%, at least about 96%, at least about 97%, at least about 98%, at least about 99%, or 100% identical to the amino acid sequence Xaa-Xaa-Cys-Xaa-Arg-Ser-Xaa-Thr-Asp-Cys-Gly-Gly-Pro-Lys-Asp-His-Pro (SEQ ID NO:1). In some embodiments, the peptide comprises an amino acid sequence that is at least about 80%, identical to the amino acid sequence according to SEQ ID NO:1. In some embodiments, the peptide comprises an amino acid sequence that is at least about 85%, identical to the amino acid sequence according to SEQ ID NO:1. In some embodiments, the peptide comprises an amino acid sequence that is at least about 90%, identical to the amino acid sequence according to SEQ ID NO:1. In some embodiments, the peptide comprises an amino acid sequence that is at least about 95%, identical to the amino acid sequence according to SEQ ID NO:1. In some embodiments, the peptide comprises an amino acid sequence that is at least about 96%, identical to the amino acid sequence according to SEQ ID NO:1. In some embodiments, the peptide comprises an amino acid sequence that is at least about 97%, identical to the amino acid sequence according to SEQ ID NO:1. In some embodiments, the peptide comprises an amino acid sequence that is at least about 98%, identical to the amino acid sequence according to SEQ ID NO:1. In some embodiments, the peptide comprises an amino acid sequence that is at least about 99%, identical to the amino acid sequence according to SEQ ID NO:1. In some embodiments, the peptide comprises an amino acid sequence according to SEQ ID NO:1. In some embodiments, the peptide consists of an amino acid sequence according to SEQ ID NO:1.

In some embodiments, the peptide comprises: Cys at a position corresponding to position 3 of SEQ ID NO:1; Arg at a position corresponding to position 5 of SEQ ID NO:1; Ser at a position corresponding to position 6 of SEQ ID NO:1; Thr at a position corresponding to position 8 of SEQ ID NO:1; Asp at a position corresponding to position 9 of SEQ ID NO:1; Cys at a position corresponding to position 10 of SEQ ID NO:1; Gly at a position corresponding to position 11 of SEQ ID NO:1; Gly at a position corresponding to position 12 of SEQ ID NO:1; Pro at a position corresponding to position 13 of SEQ ID NO:1; Lys at a position corresponding to position 14 of SEQ ID NO:1; and His at a position corresponding to position 16 of SEQ ID NO:1. In some embodiments, the peptide comprises Cys at a position corresponding to position 3 of SEQ ID NO:1. In some embodiments, the peptide comprises Arg at a position corresponding to position 5 of SEQ ID NO:1. In some embodiments, the peptide comprises Ser at a position corresponding to position 6 of SEQ ID NO:1. In some embodiments, the peptide comprises Thr at a position corresponding to position 8 of SEQ ID NO:1. In some embodiments, the peptide comprises Asp at a position corresponding to position 9 of SEQ ID NO:1. In some embodiments, the peptide comprises Cys at a position corresponding to position 10 of SEQ ID NO:1. In some embodiments, the peptide comprises Gly at a position corresponding to position 11 of SEQ ID NO:1. In some embodiments, the peptide comprises Gly at a position corresponding to position 12 of SEQ ID NO:1. In some embodiments, the peptide comprises Pro at a position corresponding to position 13 of SEQ ID NO:1. In some embodiments, the peptide comprises Lys at a position corresponding to position 14 of SEQ ID NO:1. In some embodiments, the peptide comprises His at a position corresponding to position 16 of SEQ ID NO:1.

The present disclosure also provides peptides comprising an amino acid sequence that is at least about 80%, at least about 85%, at least about 90%, at least about 95%, at least about 96%, at least about 97%, at least about 98%, at least about 99%, or 100% identical to the amino acid sequence Ala-Leu-Cys-Arg-Arg-Ser-Thr-Thr-Asp-Cys-Gly-Gly-Pro-Lys-Asp-His-Pro (SEQ ID NO:2). In some embodiments, the peptide comprises an amino acid sequence that is at least about 80%, identical to the amino acid sequence according to SEQ ID NO:2. In some embodiments, the peptide comprises an amino acid sequence that is at least about 85%, identical to the amino acid sequence according to SEQ ID NO:2. In some embodiments, the peptide comprises an amino acid sequence that is at least about 90%, identical to the amino acid sequence according to SEQ ID NO:2. In some embodiments, the peptide comprises an amino acid sequence that is at least about 95%, identical to the amino acid sequence according to SEQ ID NO:2. In some embodiments, the peptide comprises an amino acid sequence that is at least about 96%, identical to the amino acid sequence according to SEQ ID NO:2. In some embodiments, the peptide comprises an amino acid sequence that is at least about 97%, identical to the amino acid sequence according to SEQ ID NO:2. In some embodiments, the peptide comprises an amino acid sequence that is at least about 98%, identical to the amino acid sequence according to SEQ ID NO:2. In some embodiments, the peptide comprises an amino acid sequence that is at least about 99%, identical to the amino acid sequence according to SEQ ID NO:2. In some embodiments, the peptide comprises an amino acid sequence according to SEQ ID NO:2. In some embodiments, the peptide consists of an amino acid sequence according to SEQ ID NO:2. In any of these embodiments, the peptides that comprise an amino acid sequence according to SEQ ID NO:2 do not comprise a C-terminus of Leu-Thr-Ser linked directly to SEQ ID NO:2.

In some embodiments, these peptides comprise from about 17 to about 40 amino acids, from about 17 to about 38 amino acids, from about 17 to about 36 amino acids, from about 17 to about 34 amino acids, from about 17 to about 32 amino acids, from about 17 to about 30 amino acids, from about 17 to about 28 amino acids, from about 17 to about 26 amino acids, from about 17 to about 24 amino acids, from about 17 to about 22 amino acids, from about 17 to about 20 amino acids, or from about 17 to about 19 amino acids.

The present disclosure also provides peptides comprising an amino acid sequence that is at least about 80%, at least about 85%, at least about 90%, at least about 95%, at least about 96%, at least about 97%, at least about 98%, at least about 99%, or 100% identical to the amino acid sequence Xaa-Xaa-Cys-Xaa-Arg-Ser-Xaa-Thr-Asp-Cys-Gly-Gly-Pro-Lys-Asp-His-Gly-Ser-Xaa-Arg-Ser-Lys-Lys-Thr-Met-Xaa-Xaa-Gln-Lys-Asn-Xaa-Xaa-Ser-Glu (SEQ ID NO:3). In some embodiments, the peptide comprises an amino acid sequence that is at least about 80%, identical to the amino acid sequence according to SEQ ID NO:3. In some embodiments, the peptide comprises an amino acid sequence that is at least about 85%, identical to the amino acid sequence according to SEQ ID NO:3. In some embodiments, the peptide comprises an amino acid sequence that is at least about 90%, identical to the amino acid sequence according to SEQ ID NO:3. In some embodiments, the peptide comprises an amino acid sequence that is at least about 95%, identical to the amino acid sequence according to SEQ ID NO:3. In some embodiments, the peptide comprises an amino acid sequence that is at least about 96%, identical to the amino acid sequence according to SEQ ID NO:3. In some embodiments, the peptide comprises an amino acid sequence that is at least about 97%, identical to the amino acid sequence according to SEQ ID NO:3. In some embodiments, the peptide comprises an amino acid sequence that is at least about 98%, identical to the amino acid sequence according to SEQ ID NO:3. In some embodiments, the peptide comprises an amino acid sequence that is at least about 99%, identical to the amino acid sequence according to SEQ ID NO:3. In some embodiments, the peptide comprises an amino acid sequence according to SEQ ID NO:3. In some embodiments, the peptide consists of an amino acid sequence according to SEQ ID NO:3.

In some embodiments, the peptide comprises: Cys at a position corresponding to position 3 of SEQ ID NO:3; Arg at a position corresponding to position 5 of SEQ ID NO:3; Ser at a position corresponding to position 6 of SEQ ID NO:3; Thr at a position corresponding to position 8 of SEQ ID NO:3; Asp at a position corresponding to position 9 of SEQ ID NO:3; Cys at a position corresponding to position 10 of SEQ ID NO:3; Gly at a position corresponding to position 11 of SEQ ID NO:3; Gly at a position corresponding to position 12 of SEQ ID NO:3; Pro at a position corresponding to position 13 of SEQ ID NO:3; Lys at a position corresponding to position 14 of SEQ ID NO:3; Asp at a position corresponding to position 15 of SEQ ID NO:3; His at a position corresponding to position 16 of SEQ ID NO:3; Arg at a position corresponding to position 20 of SEQ ID NO:3; Ser at a position corresponding to position 21 of SEQ ID NO:3; Lys at a position corresponding to position 22 of SEQ ID NO:3; Lys at a position corresponding to position 23 of SEQ ID NO:3; Thr at a position corresponding to position 24 of SEQ ID NO:3; Met at a position corresponding to position 25 of SEQ ID NO:3; Gln at a position corresponding to position 28 of SEQ ID NO:3; Lys at a position corresponding to position 29 of SEQ ID NO:3; Asn at a position corresponding to position 30 of SEQ ID NO:3; Ser at a position corresponding to position 33 of SEQ ID NO:3; and Glu at a position corresponding to position 34 of SEQ ID NO:3. In some embodiments, the peptide comprises Cys at a position corresponding to position 3 of SEQ ID NO:3. In some embodiments, the peptide comprises Arg at a position corresponding to position 5 of SEQ ID NO:3. In some embodiments, the peptide comprises Ser at a position corresponding to position 6 of SEQ ID NO:3. In some embodiments, the peptide comprises Thr at a position corresponding to position 8 of SEQ ID NO:3. In some embodiments, the peptide comprises Asp at a position corresponding to position 9 of SEQ ID NO:3. In some embodiments, the peptide comprises Cys at a position corresponding to position 10 of SEQ ID NO:3. In some embodiments, the peptide comprises Gly at a position corresponding to position 11 of SEQ ID NO:3. In some embodiments, the peptide comprises Gly at a position corresponding to position 12 of SEQ ID NO:3. In some embodiments, the peptide comprises Pro at a position corresponding to position 13 of SEQ ID NO:3. In some embodiments, the peptide comprises Lys at a position corresponding to position 14 of SEQ ID NO:3. In some embodiments, the peptide comprises Asp at a position corresponding to position 15 of SEQ ID NO:3. In some embodiments, the peptide comprises His at a position corresponding to position 16 of SEQ ID NO:3. In some embodiments, the peptide comprises Arg at a position corresponding to position 20 of SEQ ID NO:3. In some embodiments, the peptide comprises Ser at a position corresponding to position 21 of SEQ ID NO:3. In some embodiments, the peptide comprises Lys at a position corresponding to position 22 of SEQ ID NO:3. In some embodiments, the peptide comprises Lys at a position corresponding to position 23 of SEQ ID NO:3. In some embodiments, the peptide comprises Thr at a position corresponding to position 24 of SEQ ID NO:3. In some embodiments, the peptide comprises Met at a position corresponding to position 25 of SEQ ID NO:3. In some embodiments, the peptide comprises Gln at a position corresponding to position 28 of SEQ ID NO:3. In some embodiments, the peptide comprises Lys at a position corresponding to position 29 of SEQ ID NO:3. In some embodiments, the peptide comprises Asn at a position corresponding to position 30 of SEQ ID NO:3. In some embodiments, the peptide comprises Ser at a position corresponding to position 33 of SEQ ID NO:3. In some embodiments, the peptide comprises Glu at a position corresponding to position 34 of SEQ ID NO:3.

In some embodiments, these peptides comprise from about 34 to about 60 amino acids, from about 34 to about 58 amino acids, from about 34 to about 56 amino acids, from about 34 to about 54 amino acids, from about 34 to about 52 amino acids, from about 34 to about 50 amino acids, from about 34 to about 48 amino acids, from about 34 to about 46 amino acids, from about 34 to about 44 amino acids, from about 34 to about 42 amino acids, from about 34 to about 40 amino acids, or from about 34 to about 38 amino acids.

The present disclosure also provides peptides comprising an amino acid sequence that is at least about 80%, at least about 85%, at least about 90%, at least about 95%, at least about 96%, at least about 97%, at least about 98%, at least about 99%, or 100% identical to the amino acid sequence Ala-Leu-Cys-Arg-Arg-Ser-Thr-Thr-Asp-Cys-Gly-Gly-Pro-Lys-Asp-His-Gly-Ser-Leu-Arg-Ser-Lys-Lys-Thr-Met-Leu-Val-Gln-Lys-Asn-Val-Thr-Ser-Glu (SEQ ID NO:4). In some embodiments, the peptide comprises an amino acid sequence that is at least about 80%, identical to the amino acid sequence according to SEQ ID NO:4. In some embodiments, the peptide comprises an amino acid sequence that is at least about 85%, identical to the amino acid sequence according to SEQ ID NO:4. In some embodiments, the peptide comprises an amino acid sequence that is at least about 90%, identical to the amino acid sequence according to SEQ ID NO:4. In some embodiments, the peptide comprises an amino acid sequence that is at least about 95%, identical to the amino acid sequence according to SEQ ID NO:4. In some embodiments, the peptide comprises an amino acid sequence that is at least about 96%, identical to the amino acid sequence according to SEQ ID NO:4. In some embodiments, the peptide comprises an amino acid sequence that is at least about 97%, identical to the amino acid sequence according to SEQ ID NO:4. In some embodiments, the peptide comprises an amino acid sequence that is at least about 98%, identical to the amino acid sequence according to SEQ ID NO:4. In some embodiments, the peptide comprises an amino acid sequence that is at least about 99%, identical to the amino acid sequence according to SEQ ID NO:4. In some embodiments, the peptide comprises an amino acid sequence according to SEQ ID NO:4. In some embodiments, the peptide consists of an amino acid sequence according to SEQ ID NO:4.

In some embodiments, the hCG peptide variant, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled hCG peptide variants, or fragments thereof, can be used to carry out diagnostic procedures in a variety of cell or tissue types. For imaging procedures, in vitro or in vivo, the hCG peptide variants can be labeled with additional agents, such as NMR contrasting agents, X-ray contrasting agents, or quantum dots. Methods for attaching a detectable agent to polypeptides are known in the art. The hCG peptide variants can also be attached to an insoluble support (such as a bead, a glass or plastic slide, or the like).

In some embodiments, the hCG peptide variants, or fragment thereof, can be conjugated to a therapeutic agent including, but not limited to, radioisotopes (such as $^{111}$In or $^{90}$Y), toxins (such as tetanus toxoid or ricin), toxoids, and chemotherapeutic agents.

In some embodiments, the hCG peptide variants, or fragments thereof, can be conjugated to an imaging agent. Imaging agents include, for example, a labeling moiety (such as biotin, fluorescent moieties, radioactive moieties, histidine tag or other peptide tags) for easy isolation or detection.

The hCG peptide variants described herein can be fragments of the particular complete amino acid sequence. The amino acid sequence of any individual hCG peptide variant can be missing consecutive amino acids constituting at least 20%, at least 15%, at least 10%, at least 5%, at least 4%, at least 3%, at least 2%, or at least 1%, of the particular complete amino acid sequence. The omitted consecutive amino acids may be from the C-terminus or N-terminus portion of the peptide. Alternately, the omitted consecutive amino acids may be from the internal portion of the peptide, thus retaining at least its C-terminus and N-terminus amino acids of the peptide.

The hCG peptide variants described herein can have one or more amino acid additions, deletions, or substitutions compared to the particular complete amino acid sequence. Any individual hCG peptide variant can have at least one, at least two, at least three, at least four, at least five, at least six, at least seven, at least eight, at least nine, at least ten, at least eleven, or at least twelve amino acid additions, deletions, or substitutions compared to the particular complete amino acid sequence. Any individual hCG peptide variant can have one, two, three, four, five, six, seven, eight, nine, ten, eleven, or twelve amino acid additions, deletions, or substitutions compared to the particular complete amino acid sequence. The amino acid additions, deletions, or substitutions can take place at any amino acid position within the hCG peptide variant.

Where a particular hCG peptide variant comprises at least one or more substitutions, the substituted amino acid(s) can each be, independently, any naturally occurring amino acid or any non-naturally occurring amino acid. Thus, a particular hCG peptide variant may comprise one or more amino acid substitutions that are naturally occurring amino acids and/or one or more amino acid substitutions that are non-naturally occurring amino acids. Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe. Substitutions of a member of one class with another member of the same class are contemplated herein. Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Non-naturally occurring amino acids include, for example, norleucine, omithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The hCG peptide variants which are modified as described herein retain their ability to elicit an anti-cancer response.

In some embodiments, any of the peptides described herein can be linked to a nanoparticle.

The present disclosure also provides nucleic acid molecules encoding peptides that comprise at least one or more hCG peptide variants. The present disclosure also provides nucleic acid molecules comprising a nucleotide sequence that is at least about 80%, at least about 85%, at least about 90%, at least about 95%, at least about 96%, at least about 97%, at least about 98%, or at least about 99% identical to the nucleotide sequence gcgctgtgccgccgcagcaccaccgattgc ggcggcccgaaagatcatccg (SEQ ID NO:5). In some embodiments, the nucleic acid molecule comprises a nucleotide sequence that is at least about 80% identical to the nucleotide sequence according to SEQ ID NO:5. In some embodiments, the nucleic acid molecule comprises a nucleotide sequence that is at least about 85% identical to the nucleotide sequence according to SEQ ID NO:5. In some embodiments, the nucleic acid molecule comprises a nucleotide sequence that is at least about 90% identical to the nucleotide sequence according to SEQ ID NO:5. In some embodiments, the nucleic acid molecule comprises a nucleotide sequence that is at least about 95% identical to the nucleotide sequence according to SEQ ID NO:5. In some embodiments, the nucleic acid molecule comprises a nucleotide sequence that is at least about 96% identical to the nucleotide sequence according to SEQ ID NO:5. In some embodiments, the nucleic acid molecule comprises a nucleotide sequence that is at least about 97% identical to the nucleotide sequence according to SEQ ID NO:5. In some embodiments, the nucleic acid molecule comprises a nucleotide sequence that is at least about 98% identical to the nucleotide sequence according to SEQ ID NO:5. In some embodiments, the nucleic acid molecule comprises a nucleotide sequence that is at least about 99% identical to the nucleotide sequence according to SEQ ID NO:5. In some embodiments, the nucleic acid molecule comprises a nucleotide sequence according to SEQ ID NO:5. In some embodiments, the nucleic acid molecule consists of a nucleotide sequence according to SEQ ID NO:5.

In some embodiments, these nucleic acid molecules comprise from about 51 to about 120 nucleobases, from about 51 to about 114 nucleobases, from about 51 to about 108 nucleobases, from about 51 to about 102 nucleobases, from about 51 to about 96 nucleobases, from about 51 to about 90 nucleobases, from about 51 to about 84 nucleobases, from about 51 to about 78 nucleobases, from about 51 to about 72 nucleobases, from about 51 to about 66 nucleobases, from about 51 to about 60 nucleobases, or from about 51 to about 54 nucleobases.

The present disclosure also provides nucleic acid molecules comprising a nucleotide sequence that is at least about 80%, at least about 85%, at least about 90%, at least about 95%, at least about 96%, at least about 97%, at least about 98%, or at least about 99% identical to the nucleotides sequence gcgctgtgccgccgcagcaccaccgattgcggcggcccgaaagatcatggcagcctgcgcagcaaaaa aaccatgctggtgcagaaaaacgtgaccagcgaa (SEQ ID NO:6). In some embodiments, the nucleic acid molecule comprises a nucleotide sequence that is at least about 80% identical to the nucleotides sequence according to SEQ ID NO:6. In some embodiments, the nucleic acid molecule comprises a nucleotide sequence that is at least about 85% identical to the nucleotides sequence according to SEQ ID NO:6. In some embodiments, the nucleic acid molecule comprises a nucleotide sequence that is at least about 90% identical to the nucleotides sequence according to SEQ ID NO:6. In some embodiments, the nucleic acid molecule comprises a nucleotide sequence that is at least about 95% identical to the nucleotides sequence according to SEQ ID NO:6. In some embodiments, the nucleic acid molecule comprises a nucleotide sequence that is at least about 96% identical to the nucleotides sequence according to SEQ ID NO:6. In some embodiments, the nucleic acid molecule comprises a nucleotide sequence that is at least about 97% identical to the nucleotides sequence according to SEQ ID NO:6. In some embodiments, the nucleic acid molecule comprises a nucleotide sequence that is at least about 98% identical to the nucleotides sequence according to SEQ ID NO:6. In some embodiments, the nucleic acid molecule comprises a nucleotide sequence that is at least about 99% identical to the nucleotides sequence according to SEQ ID NO:6. In some embodiments, the nucleic acid molecule comprises a nucleotide sequence according to SEQ ID NO:6. In some embodiments, the nucleic acid molecule consists of a nucleotide sequence according to SEQ ID NO:6.

In some embodiments, the nucleic acid molecule comprises from about 102 to about 140 nucleobases, from about 102 to about 136 nucleobases, from about 102 to about 132 nucleobases, from about 102 to about 128 nucleobases, from about 102 to about 124 nucleobases, from about 102 to about 120 nucleobases, from about 102 to about 116 nucleobases, from about 102 to about 112 nucleobases, or from about 102 to about 108 nucleobases.

In some embodiments, the nucleic acid molecule encoding any particular hCG peptide variant can be a bacterial codon optimized sequence (such as an *E. coli* optimized sequence) or a mammalian optimized sequence (such as a human optimized sequence). The *E. coli* optimized sequences can be used, for example, to produce peptides. The human optimized sequences can be used in, for example, viral vectors. Methods of codon optimization (whether for bacterial or mammalian) are well known to the skilled artisan. In some embodiments, coding sequences can be optimized for stability and high levels of expression. In some instances, codons are selected to reduce secondary structure formation of the RNA such as that formed due to intramolecular bonding.

The specific sequences recited herein are simply one example of a nucleic acid molecule that can encode a particular hCG peptide variant. One skilled in the art having knowledge of the genetic code can routinely prepare and design a plethora of nucleic acid molecules encoding the same hCG peptide variant. The length and nucleotide content of any particular nucleic acid molecule is dictated by the desired amino acid sequence of the encoded hCG peptide variant. The nucleic acid molecule sequences shown herein are DNA, although RNA nucleic acid molecules are also contemplated.

The present disclosure also provides pharmaceutical compositions comprising at least one of the nucleic acid molecules or peptides described herein and a pharmaceutically acceptable carrier.

In some embodiments, the pharmaceutical composition further comprises a chemotherapeutic agent. In some embodiments, the chemotherapeutic agent is tamoxifen. In some embodiments, the chemotherapeutic agent is a histone deacetylase inhibitor. In some embodiments, the histone deacetylase inhibitor is chosen from suberanilohydroxamic acid (Vorinostat, Zolinza®); Romidepsin (Istodax®); Chidamide (Epidaza®); Panobinostat (Farydak®); Belinostat (PXD101; Beleodaq®); Valproic acid (Depakote® and Epilim®); N-(2-aminophenyl)-4-[[(4-pyridin-3-ylpyrimidin-2-yl)amino]methyl]benzamide (Mocetinostat, MGCD0103); 3-[(dimethylamino)methyl]-N-{2-[4-(hydroxycarbamoyl)phenoxy]ethyl}-1-benzofuran-2-carboxamide (Abexinostat, PCI-24781); pyridin-3-ylmethyl N-[[4-[(2-aminophenyl) carbamoyl]phenyl]methyl]carbamate (Entinostat, MS-275); (E)-3-(2-butyl-1-(2-(diethylamino)ethyl)-1H-benzo[d]imidazol-5-yl)-N-hydroxyacrylamide (Pracinostat, SB939); (2E)-3-[1-({4-[(dimethylamino)methyl]phenyl} sulfonyl)-1H-pyrrol-3-yl]-N-hydroxyacrylamide (Resminostat, 4SC-201); [6-(diethylamino methyl) naphthalen-2-yl]methyl N-[4-(hydroxycarbamoyl)phenyl]carbamate (Givinostat, ITF2357); N-hydroxy-2-[4-[[(1-methylindol-3-yl)methylamino]methyl]piperidin-1-yl]pyrimidine-5-carboxamide (Quisinostat, JNJ-26481585); and N-(2-amino-5-fluorophenyl)-4-[[[1-oxo-3-(3-pyridinyl)-2-propen-1-yl]amino]methyl]-benzamide (HBI-8000, Epidaza). In some embodiments, the chemotherapeutic agent is an anti-methylation agent. In some embodiments, the anti-methylation agent is azacitidine or decitabine.

A pharmaceutically acceptable carrier refers to at least one component of a pharmaceutical preparation that is normally used for administration of active ingredients. As such, a carrier can contain any pharmaceutical excipient used in the art and any form of vehicle for administration. Carriers include, but are not limited to, phosphate buffered saline, physiological saline, water, citrate/sucrose/Tween formulations and emulsions such as, for example, oil/water emulsions.

The compositions can also include an active therapeutic agent and a variety of other pharmaceutically acceptable components. See Remington's Pharmaceutical Science (15th ed., Mack Publishing Company, Easton, Pa. (1980)). The desired form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™) hydroxypropyl methylcellulose, sucrose, starch, and ethylcellulose. Lubricants that can be used include magnesium stearates, stearic acid, silicone fluid, talc, waxes, oils, and colloidal silica. Additional excipients include, for example, colorants, taste-masking agents, solubility aids, suspension agents, compressing agents, enteric coatings, sustained release aids, and the like.

In some embodiments, the compositions can be administered in the form of a depot injection or implant preparation, which can be formulated in such a manner as to permit a sustained release. An exemplary composition comprises any one or more of the compositions described herein formulated in aqueous buffer.

In some embodiments, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, aerosols, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base. Some examples of formulations of a composition for topical use include, but are not limited to, drops, tinctures, lotions, creams, solutions, and ointments containing the active ingredient and various supports and vehicles.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

The present disclosure also provides vectors comprising at least one of the nucleic acid molecules described herein. The vector can be capable of expressing any of the hCG peptide variants described herein. In some embodiments, the vector is a recombinant vector. In some embodiments, the vector is a plasmid. In some embodiments, the plasmid is a DNA plasmid. The vector can be useful for transfecting cells with a nucleic acid molecule encoding an hCG peptide variant, wherein the transformed host cell is cultured and maintained under conditions wherein expression of the peptide takes place.

In some embodiments, the vectors can comprise regulatory elements for gene expression of the coding sequences of the nucleic acid. The regulatory elements can be a promoter, an enhancer an initiation codon, a stop codon, or a polyadenylation signal. In some embodiments, the vector can comprise heterologous nucleic acid encoding an hCG peptide variant and can further comprise an initiation codon, which is upstream of the peptide coding sequence, and a stop codon, which is downstream of the peptide coding sequence. The initiation and termination codon are in frame with the peptide coding sequence.

The vector can also comprise a promoter that is operably linked to the peptide coding sequence. The promoter operably linked to the hCG peptide variant coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter, or the like. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Representative examples of promoters include the bacteriophage T7 promoter, bacteriophage T3 promoter, SP6 promoter, lac operator-promoter, tac promoter, mycobacterial Hsp60 promoter, SV40 late promoter, SV40 early promoter, RSV-LTR promoter, CMV IE promoter, SV40 early promoter or SV40 late promoter and the CMV IE promoter.

The vector can also comprise a polyadenylation signal, which can be downstream of the peptide coding sequence. The polyadenylation signal can be a SV40 polyadenylation signal, LTR polyadenylation signal, CMV polyadeylation signal, bovine growth hormone (bGH) polyadenylation signal, human growth hormone (hGH) polyadenylation signal, or human (3-globin polyadenylation signal. The SV40 polyadenylation signal can be a polyadenylation signal from a pCEP4 vector (Invitrogen, San Diego, Calif.).

The vector can also comprise an enhancer upstream of the consensus BoNT-A, BoNT-B, BoNT-E, and BoNT-F peptide sequences. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration.

The vector can also comprise a regulatory sequence, which can be well suited for gene expression in a mammalian or human cell into which the vector is administered. The consensus coding sequence can comprise a codon, which can allow more efficient transcription of the coding sequence in the host cell.

The vector can be pSE420 (Invitrogen, San Diego, Calif.) or pET28b (EMD Millipore, Billerca, Mass.), which can be used for protein production in *E. coli*. The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989).

In some embodiments, the vector is a viral vector. Suitable viral vectors include, but are not limited to, an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and cytomegalovirus (CMV) vector. Suitable adenovirus vectors include, but are not limited to, adenovirus 4 and adenovirus 5. A suitable vaccinia virus vector includes, but is not limited to, modified vaccinia Ankara (MVA). Suitable paramyxovirus vectors include, but are not limited to, modified parainfluenza virus (PIV2) and recombinant human parainfluenza virus (rHPIV2). Suitable CMV vectors include, but are not limited to, Rhesus Macaque CMV (RhCMV) vectors and Human CMV (HCMV) vectors. In some embodiments, the vector is present within a composition comprising a pharmaceutically acceptable carrier. One skilled in the art is readily familiar with numerous vectors, many of which are commercially available.

In some embodiments, the vector is a non-viral vector. In some embodiments, the non-viral vector is RNA, such as mRNA. In some embodiments, the mRNA is protamine-complexed mRNA, wherein the hCG peptide variant or peptide is encoded by the mRNA, and the protamine complexes contribute a strong anti-cancer signal. An exemplary mRNA vector platform is RNActive® (CureVac Inc).

The present disclosure also provides host cells comprising any of the vectors described herein. The host cells can be used, for example, to express the hCG peptide variants, or fragments thereof. The hCG peptide variants, or fragments thereof, can also be expressed in cells in vivo. The host cell that is transformed (for example, transfected) to produce the hCG peptide variants, or fragments thereof, can be an immortalised mammalian cell line, such as those of lymphoid origin (for example, a myeloma, hybridoma, trioma or quadroma cell line). The host cell can also include normal lymphoid cells, such as B-cells, that have been immortalized by transformation with a virus (for example, the Epstein-Barr virus).

In some embodiments, the host cells include, but are not limited to: bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, Conn.)), *Drosophila* S2 cells and *Trichoplusia* in High Five® Cells (Invitrogen, Carlsbad, Calif.); and mammalian cells, such as COS1 and COS7 cells, Chinese hamster ovary (CHO) cells, NSO myeloma cells, NIH 3T3 cells, 293 cells, Procell92S, perC6, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, Va.) and the National Institute of General Medical Sciences (NIGMS) Human Genetic Cell Repository at the Coriell Cell Repositories (Camden, N.J.). These cell types are only representative and are not meant to be an exhaustive list.

Among other considerations, some of which are described above, a host cell strain may be chosen for its ability to process the expressed hCG peptide variants, or fragment thereof, in the desired fashion. Post-translational modifications of the polypeptide include, but are not limited to, glycosylation, acetylation, carboxylation, phosphorylation, lipidation, and acylation, and it is an aspect of the present disclosure to provide hCG peptide variants thereof with one or more of these post-translational modifications.

The present disclosure also provides kits comprising any of the hCG peptide variants, fragments thereof, peptides, nucleic acid molecules, vectors, or cells, described herein. The kit can include, for example, container(s), package(s) or dispenser(s) along with labels and instructions for administration or use.

The present disclosure also provides methods for treating a subject having cancer comprising administering to the subject in need thereof at least one peptide described herein, wherein the cancer is selected from the group consisting of breast cancer, prostate cancer, ovarian cancer, uterine cancer, endometrial cancer, brain cancer, and testicular cancer.

The present disclosure also provides methods for treating a subject having cancer comprising administering to the subject in need thereof at least one nucleic acid molecule described herein, wherein the cancer is selected from the group consisting of breast cancer, prostate cancer, ovarian cancer, uterine cancer, endometrial cancer, brain cancer, and testicular cancer.

The present disclosure also provides methods for treating a subject having cancer comprising administering to the subject in need thereof any of the pharmaceutical compositions described herein, wherein the cancer is selected from the group consisting of breast cancer, prostate cancer, ovarian cancer, uterine cancer, endometrial cancer, brain cancer, and testicular cancer.

The methods described herein can be used as a prophylactic or therapeutic cancer treatment.

In some embodiments, the peptides, nucleic acid molecules, and/or compositions can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. Alternately, the compositions can be administered to a subject by routes including oral, nasal, ophthalmic, rectal, or topical. The most typical route of administration is intravascular, subcutaneous, or intramuscular, although other routes can be effective. In some embodiments, compositions are administered as a sustained release composition or device, such as a Medipad™ device. The composition can also be administered via the respiratory tract, for example, using a dry powder inhalation device, nebulizer, or a metered dose inhaler. The composition can also be administered by traditional syringes, needleless injection devices, "microprojectile bombardment gone guns," or other physical methods such as electroporation, "hydrodynamic method", or ultrasound.

In some embodiments, any of the hCG peptide variants, constructs, vectors, or cells described herein, or compositions comprising the same, can be combined into a single therapeutic or prophylactic regimen.

Effective doses of the compositions of the present disclosure, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

In some embodiments, the composition can be administered to a subject by sustained release administration, by such means as depot injections of erodible implants directly applied during surgery or by implantation of an infusion pump or a biocompatible sustained release implant into the subject. Alternately, the composition can be administered to a subject by injectable depot routes of administration, such as by using 1-, 3-, or 6-month depot injectable or biodegradable materials and methods, or by applying to the skin of the subject a transdermal patch containing the composition, and leaving the patch in contact with the subject's skin, generally for 1 to 5 hours per patch.

In some embodiments, the compositions comprise about 1 nanogram to about 10 mg of nucleic acid or peptide. In some embodiments, the compositions comprise: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg.

In some embodiments, the compositions comprise about 5 nanograms to about 10 mg of nucleic acid molecule or peptide. In some embodiments, the compositions comprise about 25 nanograms to about 5 mg of nucleic acid molecule or peptide. In some embodiments, the compositions contain about 50 nanograms to about 1 mg of nucleic acid molecule or peptide. In some embodiments, the compositions contain about 0.1 to about 500 micrograms of nucleic acid molecule or peptide. In some embodiments, the compositions contain about 1 to about 350 micrograms of nucleic acid molecule or peptide. In some embodiments, the compositions contain about 5 to about 250 micrograms of nucleic acid molecule or peptide. In some embodiments, the compositions contain about 10 to about 200 micrograms of nucleic acid molecule or peptide. In some embodiments, the compositions contain about 15 to about 150 micrograms of nucleic acid molecule or peptide. In some embodiments, the compositions contain about 20 to about 100 micrograms of nucleic acid molecule or peptide. In some embodiments, the compositions contain about 25 to about 75 micrograms of nucleic acid molecule or peptide. In some embodiments, the compositions contain about 30 to about 50 micrograms of nucleic acid molecule or peptide. In some embodiments, the compositions contain about 35 to about 40 micrograms of nucleic acid molecule or peptide. In some embodiments, the compositions contain about 100 to about 200 micrograms of nucleic acid molecule or peptide. In some embodiments, the compositions comprise about 10 to about 100 micrograms of nucleic acid molecule or peptide. In some embodiments, the compositions comprise about 20 to about 80 micrograms of nucleic acid molecule or peptide. In some embodiments, the compositions comprise about 25 to about 60 micrograms of nucleic acid molecule or peptide. In some embodiments, the compositions comprise about 30 nanograms to about 50 micrograms of nucleic acid molecule or peptide. In some embodiments, the compositions comprise about 35 nanograms to about 45 micrograms of nucleic acid molecule or peptide. In some embodiments, the compositions contain about 0.1 to about 500 micrograms of nucleic acid molecule or peptide. In some embodiments, the compositions contain about 1 to about 350 micrograms of nucleic acid molecule or peptide. In some embodiments, the compositions contain about 25 to about 250 micrograms of nucleic acid molecule or peptide. In some embodiments, the compositions contain about 100 to about 200 micrograms of nucleic acid molecule or peptide.

The compositions can be formulated according to the mode of administration to be used. In cases where compositions are injectable pharmaceutical compositions, they are sterile, pyrogen free and particulate free. An isotonic formulation can be used. Generally, additives for isotonicity can include sodium chloride, dextrose, mannitol, sorbitol and lactose. In some cases, isotonic solutions such as phosphate buffered saline are suitable. Stabilizers include gelatin and albumin. In some embodiments, a vasoconstriction agent is added to the formulation.

The compositions can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalane, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more suitably, the poly-L-glutamate is present in the composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalane, and hyaluronic acid can also be used administered in conjunction with the genetic construct. In some embodiments, the plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In some embodiments, the transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The peptides and compositions described herein can be used to treat or prevent cancer. In some embodiments, the method comprises administering to a human a therapeutically- or prophylactically-effective amount of any of the peptides or compositions described herein such that the cancer is diminished or prevented. In some embodiments, the subject being treated will have been previously diagnosed as having cancer. Such subjects will, thus, have been diagnosed as being in need of such treatment. Alternately, the treatment may be intended to prevent cancer in a subject that does not yet have cancer.

In some embodiments, the subject(s) that can be treated by the above-described methods is an animal, including mammals and non-mammals. Suitable mammals, include, but are not limited to, humans, non-human primates, rodents (including rats, mice, hamsters and guinea pigs) cow, horse, sheep, badger, opossum, goat, pig, dog and cat. In most instances, the mammal is a human. In some embodiments, the non-mammal is a fish.

The present disclosure also provides hCG peptide variants for use in the preparation of a medicament for treating or preventing cancer, wherein the peptide variant is any of the hCG peptide variants described herein.

The present disclosure also provides hCG peptide variants for use in treating or preventing cancer, wherein the peptide variant is any of the hCG peptide variants described herein.

The present disclosure also provides uses of an hCG peptide variant in the preparation of a medicament for treating or preventing cancer, wherein the peptide is any of the hCG peptide variants described herein.

The present disclosure also provides uses of an hCG peptide variant in treating or preventing cancer, wherein the peptide variant is any of the hCG peptide variants described herein.

The present disclosure also provides compositions for use in the preparation of a medicament for treating or preventing cancer, wherein the composition comprises any of the hCG peptide variants described herein.

The present disclosure also provides compositions for use in treating or preventing cancer, wherein the composition comprises any of the hCG peptide variants described herein.

The present disclosure also provides uses of compositions in the preparation of a medicament for treating or preventing cancer, wherein the composition comprises any of the hCG peptide variants described herein.

The present disclosure also provides compositions in treating or preventing cancer, wherein the compositions comprises any of the hCG peptide variants described herein.

The present disclosure also provides hCG nucleic acid molecules for use in the preparation of a medicament for treating or preventing cancer, wherein the nucleic acid molecule encodes any of the hCG peptide variants described herein.

The present disclosure also provides hCG nucleic acid molecules for use in treating or preventing cancer, wherein the nucleic acid molecule encodes any of the hCG peptide variants described herein.

The present disclosure also provides uses of hCG nucleic acid molecules in the preparation of a medicament for treating or preventing cancer, wherein the nucleic acid molecule encodes any of the hCG peptide variants described herein.

The present disclosure also provides uses of hCG nucleic acid molecules in treating or preventing cancer, wherein the nucleic acid molecule encodes any of the hCG peptide variants described herein.

The present disclosure also provides compositions for use in the preparation of a medicament for treating or preventing cancer, wherein the composition comprises at least one nucleic acid molecule that encodes any of the hCG peptide variants described herein.

The present disclosure also provides compositions for use in treating or preventing cancer, wherein the composition comprises at least one nucleic acid molecule that encodes any of the hCG peptide variants described herein.

The present disclosure also provides uses of a composition in the preparation of a medicament for treating or preventing cancer, wherein the composition comprises at least one nucleic acid molecule that encodes any of the hCG peptide variants described herein.

The present disclosure also provides uses of a composition in treating or preventing cancer, wherein the composition comprises at least one nucleic acid molecule that encodes any of the hCG peptide variants described herein.

Various modifications of the described subject matter, in addition to those described herein, will be apparent to those skilled in the art from the foregoing description. Such modifications are also intended to fall within the scope of the appended claims Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for treating a subject having breast cancer comprising administering to the subject in need thereof at least one peptide comprising at least 90% identity to the amino acid sequence Xaa-Xaa-Cys-Xaa-Arg-Ser-Xaa-Thr-Asp-Cys-Gly-Gly-Pro-Lys-Asp-His-Gly-Ser-Xaa-Arg-Ser-Lys-Lys-Thr-Met-Xaa-Xaa-Gln-Lys-Asn-Xaa-Xaa-Ser-Glu (SEQ ID NO:3).

2. The method according to claim 1, wherein the administration route is selected from the group consisting of oral administration, intransal administration, intravenous administration, sublingual administration, transdermal administration, dermal administration, intraperitoneal administration, intramuscular administration, intra-tumor administration, and administration via a controlled release pump.

3. The method according to claim 1, wherein the at least one peptide comprises at least 90% identity to the amino acid sequence Ala-Leu-Cys-Arg-Arg-Ser-Thr-Thr-Asp-Cys-Gly-Gly-Pro-Lys-Asp-His-Gly-Ser-Leu-Arg-Ser-Lys-Lys-Thr-Met-Leu-Val-Gln-Lys-Asn-Val-Thr-Ser-Glu (SEQ ID NO:4).

4. The method according to claim 1, wherein the peptide is linked to a nanoparticle.

5. The method according to claim 1, further comprising administering to the subject a chemotherapeutic agent.

6. The method according to claim 5, wherein the chemotherapeutic agent is tamoxifen.

7. The method according to claim 5, wherein the chemotherapeutic agent is a histone deacetylase inhibitor.

8. The method according to claim 7, wherein the histone deacetylase inhibitor is selected from the group consisting of suberanilohydroxamic acid; Romidepsin; Chidamide; Panobinostat; Belinostat; Valproic acid; N-(2-aminophenyl)-4-[[(4-pyridin-3-ylpyrimidin-2-yl)amino]methyl]benzamide; 3-[(dimethylamino)methyl]-N-{2-[4-(hydroxycarbamoyl)phenoxy] ethyl}-1-benzofuran-2-carboxamide; pyridin-3-ylmethyl N-[[4-[(2-aminophenyl) carbamoyl]phenyl]methyl]carbamate; (E)-3-(2-butyl-1-(2-(diethylamino) ethyl)-1H-benzo[d]imidazol-5-yl)-N-hydroxyacrylamide; (2E)-3-[1-({4-[(dimethylamino)methyl]phenyl} sulfonyl)-1 H-pyrrol-3-yl]-N-hydroxyacrylamide; [6-(diethylamino methyl)naphthalen-2-yl]methyl N-[4-(hydroxycarbamoyl) phenyl]carbamate; N-hydroxy-2-[4-[[(1-methylindol-3yl) methylamino]methyl]piperidin-1-yl] pyrimidine-5-carboxamide; and N-(2-amino-5-fluorophenyl)-4-[[[1-oxo-3-(3-pyridinyl)-2-propen-1-yl]amino]methyl]-benzamide.

9. The method according to claim 5, wherein the chemotherapeutic agent is an anti-methylation agent.

10. The method according to claim 9, wherein the anti-methylation agent is azacitidine or decitabine.

* * * * *

SEQUENCE LISTING

```
<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: hCG variant
<220> FEATURE:
<221> NAME/KEY: MOD_RES
<222> LOCATION: (1)..(2)
<223> OTHER INFORMATION: Xaa is any amino acid
<220> FEATURE:
<221> NAME/KEY: MOD_RES
<222> LOCATION: (4)..(4)
<223> OTHER INFORMATION: Xaa is any amino acid
<220> FEATURE:
<221> NAME/KEY: MOD_RES
<222> LOCATION: (7)..(7)
<223> OTHER INFORMATION: Xaa is any amino acid
```

<400> SEQUENCE: 1

Xaa Xaa Cys Xaa Arg Ser Xaa Thr Asp Cys Gly Gly Pro Lys Asp His
1               5                   10                  15

Pro

<210> SEQ ID NO 2
<211> LENGTH: 17
<212> TYPE: PRT
<213> ORGANISM: Artificial Sequence
<220> FEATURE:
<223> OTHER INFORMATION: hCG variant

<400> SEQUENCE: 2

Ala Leu Cys Arg Arg Ser Thr Thr Asp Cys Gly Gly Pro Lys Asp His
1               5                   10                  15

Pro

<210> SEQ ID NO 3
<211> LENGTH: 34
<212> TYPE: PRT
<213> ORGANISM: Artificial Sequence
<220> FEATURE:
<223> OTHER INFORMATION: hCG variant
<220> FEATURE:
<221> NAME/KEY: MOD_RES
<222> LOCATION: (1)..(2)
<223> OTHER INFORMATION: Xaa is any amino acid
<220> FEATURE:
<221> NAME/KEY: MOD_RES
<222> LOCATION: (4)..(4)
<223> OTHER INFORMATION: Xaa is any amino acid
<220> FEATURE:
<221> NAME/KEY: MOD_RES
<222> LOCATION: (7)..(7)
<223> OTHER INFORMATION: Xaa is any amino acid
<220> FEATURE:
<221> NAME/KEY: MOD_RES
<222> LOCATION: (19)..(19)
<223> OTHER INFORMATION: Xaa is any amino acid
<220> FEATURE:
<221> NAME/KEY: MOD_RES
<222> LOCATION: (26)..(27)
<223> OTHER INFORMATION: Xaa is any amino acid
<220> FEATURE:
<221> NAME/KEY: MOD_RES
<222> LOCATION: (31)..(32)
<223> OTHER INFORMATION: Xaa is any amino acid

<400> SEQUENCE: 3

Xaa Xaa Cys Xaa Arg Ser Xaa Thr Asp Cys Gly Gly Pro Lys Asp His
1               5                   10                  15

Gly Ser Xaa Arg Ser Lys Lys Thr Met Xaa Xaa Gln Lys Asn Xaa Xaa
            20                  25                  30

Ser Glu

<210> SEQ ID NO 4
<211> LENGTH: 34
<212> TYPE: PRT
<213> ORGANISM: Artificial Sequence
<220> FEATURE:
<223> OTHER INFORMATION: hCG variant

<400> SEQUENCE: 4

Ala Leu Cys Arg Arg Ser Thr Thr Asp Cys Gly Gly Pro Lys Asp His
1               5                   10                  15

Gly Ser Leu Arg Ser Lys Lys Thr Met Leu Val Gln Lys Asn Val Thr

-continued

```
                20                  25                  30
Ser Glu

<210> SEQ ID NO 5
<211> LENGTH: 51
<212> TYPE: DNA
<213> ORGANISM: Artificial Sequence
<220> FEATURE:
<223> OTHER INFORMATION: hCG variant

<400> SEQUENCE: 5
gcgctgtgcc gccgcagcac caccgattgc ggcggcccga aagatcatcc g          51

<210> SEQ ID NO 6
<211> LENGTH: 102
<212> TYPE: DNA
<213> ORGANISM: Artificial Sequence
<220> FEATURE:
<223> OTHER INFORMATION: hCG variant

<400> SEQUENCE: 6
gcgctgtgcc gccgcagcac caccgattgc ggcggcccga aagatcatgg cagcctgcgc    60
agcaaaaaaa ccatgctggt gcagaaaaac gtgaccagcg aa                      102
```